(12) United States Patent
Biswas et al.

(10) Patent No.: US 6,168,797 B1
(45) Date of Patent: Jan. 2, 2001

(54) FABF

(75) Inventors: Sanjoy Biswas, Paoli; Martin K R Burnham, Barto; Jason C Fedon, Strafford; David J Holmes, West Chester; Karen A Ingraham, Auburn; Howard Kallender, Wayne; John T Lonsdale, Exton; Marie J Mazzulla, Collegeville; Karen M O'Dwyer, Phoenixville; Leslie M Palmer, Audubon; Chi Young So, Havertown; Christopher M Traini, Media; Glenn S Van Aller, Mt Penn; Stephanie Van Horn, Pottstown; Magdalena Zalacain, West Chester, all of PA (US)

(73) Assignee: SmithKline Beecham Corporation, Philadelphia, PA (US)

( * ) Notice: Under 35 U.S.C. 154(b), the term of this patent shall be extended for 0 days.

(21) Appl. No.: 09/376,689

(22) Filed: Aug. 18, 1999

(51) Int. Cl.⁷ .................................................. A61K 39/09
(52) U.S. Cl. ..................... 424/244.1; 424/234.1; 424/185.1; 424/190.1; 424/192.1; 424/200.1; 530/350; 435/69.1; 435/69.3; 435/69.7; 435/71.1; 435/183; 536/23.7

(58) Field of Search .............................. 424/244.1, 234.1, 424/185.1, 190.1, 192.1, 200.1; 530/350; 435/69.1, 69.3, 69.7, 71.1, 183; 536/23.7

(56) References Cited

U.S. PATENT DOCUMENTS

| 5,783,432 | * | 7/1998 | Gentry et al. | 435/183 |
| 5,827,689 | * | 10/1998 | Gentry et al. | 435/69.1 |

OTHER PUBLICATIONS

Edwards et al. FEBS LETT. 402(1): 62–66, 1997.*

* cited by examiner

Primary Examiner—Jennifer Graser
(74) Attorney, Agent, or Firm—Edward R. Gimmi; William T. King; Thomas S. Deibert

(57) ABSTRACT

The invention provides fabF polypeptides and polynucleotides encoding fabF polypeptides and methods for producing such polypeptides by recombinant techniques. Also provided are methods for utilizing fabF polypeptides to screen for antibacterial compounds.

6 Claims, No Drawings

FABF

FIELD OF THE INVENTION

This invention relates to newly identified polynucleotides and polypeptides, and their production and uses, as well as their variants, agonists and antagonists, and their uses. In particular, the invention relates to polynucleotides and polypeptides of the fabF family, as well as their variants, herein referred to as "fabF," "fabF polynucleotide(s)," and "fabF polypeptide(s)" as the case may be.

BACKGROUND OF THE INVENTION

The pathway for the biosynthesis of saturated fatty acids is very similar in prokaryotes and eukaryotes. However, whilst the chemical reactions may not vary, the organization of the biosynthetic apparatus is very different. Vertebrates and yeasts possess type I fatty acid synthases (FASs) in which all of the enzymatic activities are encoded on one or two polypeptide chains, respectively. The acyl carrier protein (ACP) is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs. There therefore appears to be considerable potential for selective inhibition of the bacterial systems by broad spectrum antibacterial agents (Rock, C. & Cronan, J. 1996. *Biochimica et Biophysica Acta* 1302, 1–16; Jackowski, S. 1992. In *Emerging Targets in Antibacterial and Antifungal Chemotherapy.* Ed. J. Sutcliffe & N. Georgopapadakou. Chapman & Hall, New York; Jackowski, S. et al. (1989). *J. Biol. Chem.* 264, 7624–7629.)

The first step in the biosynthetic cycle is the condensation of malonyl-ACP with acetyl-CoA by FabH. Prior to this, malonyl-ACP is synthesized from ACP and malonyl-CoA by FabD, malonyl CoA:ACP transacylase. In subsequent rounds malonyl-ACP is condensed with the growing-chain acyl-ACP (FabB and FabF, synthases I and II respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP (Heath, et al, (1996), *J. Biol. Chem.* 271, 1833–1836).

Cerulenin and thiolactomycin are potent and selective inhibitors of bacterial fatty acid biosynthesis. Extensive work with these inhibitors has proved that this biosynthetic pathway is essential for bacterial viability. No marketed antibiotics are targeted against fatty acid biosynthesis, therefore it is unlikely that novel antibiotics would be rendered inactive by known antibiotic resistance mechanisms. There is an unmet need for developing new classes of antibiotic compounds, such as those that target FabF.

FabF enzymes are of interest as potential targets for antibacterial agents.

It is particularly preferred to employ streptococcal genes and gene products as targets for the development of antibiotics. The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago *Streptococcus pneumoniae* has been one of the more intensively studied microbes. For example, much of our early understanding that DNA is, in fat the genetic material was predicated on the work of Griffith and of Avery, Macleod and McCarty using this microbe. Despite the vast amount of research with *S. pneumoniae,* many questions concerning the virulence of this microbe remain. It is particularly preferred to employ Streptococcal genes and gene products as targets for the development of antibiotics.

The frequency of *Streptococcus pneumoniae* infections has risen dramatically in the past few decades. This has been attributed to the emergence of multiply antibiotic resistant strains and an increasing population of people with weakened immune systems. It is no longer uncommon to isolate *Streptococcus pneumoniae* strains that are resistant to some or all of the standard antibiotics. This phenomenon has created an unmet medical need and demand for new antimicrobial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides and polypeptides, such as the fabF embodiments of the invention, that have a present benefit of; among other things, being useful to screen compounds for antimicrobial activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

SUMMARY OF THE INVENTION

The present invention relates to fabF, in particular fabF polypeptides and fabF polynucleotides, recombinant materials and methods for their production. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting fabF expression or activity.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to fabF polypeptides and polynucleotides as described in greater detail below. In particular, the invention relates to polypeptides and polynucleotides of a fabF of *Streptococcus pneumoniae,* that is related by amino acid sequence homology to fabF polypeptide. The invention relates especially to fabF having a nucleotide and amino acid sequences set out in Table 1 as SEQ ID NO:1 and SEQ ID NO:2 respectively. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1 fabF Polynucleotide and Polypeptide Sequences (A) *Streptococcus pneumoniae* fabF polynucleotide sequence [SEQ ID NO:1].
5'-
ATGAAACTAAATCGAGTAGTGGTAACAGGTTATGGAGTAACATCTCCAATCGGAAATACACCAGAAGAATTT
TGGAATAG TTTAGCAACTGGGAAAATCGGCATTGGTGGCATTACAAAATTTGATCATAGTGACTTTGATGTGCATAATGC
GGCAGAAA TCCAAGATTTTCCGTTCGATAAATACTTTGTAAAAAAAGATACCAACCGTTTTGATAACTATTCTTTATATG
CCTTGTAT GCAGCCCAAGAGGCTGTAAATCATGCCAATCTTGATGTAGAGGCTCTTAATAGGGATCGTTTTGGTGTTATC
GTTGCATC TGGTATTGGTGGAATCAAGGAAATTGAAGATCAGGTACTTCGCCTTCATGAAAAAGGACCCAAACGTGTCAA
ACCAATGA CTCTTCCAAAAGCTTTACCAAATATGGCTTCTGGGAATGTAGCCATGCGTTTTGGTGCAAACGGTGTTTGTA
AATCTATC AATACTGCCTGCTCTTCATCAAATGATGCGATTGGGGATGCCTTCCGCTCCATTAAGTTTGGTTTCCAAGAT
GTGATGTT GGTGGGAGGAACAGAAGCTTCTATCACACCTTTTGCCATCGCTGGTTTCCAAGCCTTAACAGCTCTCTCTAC
TACAGAGG ATCCAACTCGTGCTTCGATCCCATTTGATAAGGATCGCAATGGGTTTGTTATGGGTGAAGGTTCAGGGATGT
TGGTTCTA GAAAGTCTTGAACACGCTGAAAAACGTGGAGCTACTATCCTGGCTGAAGTGGTTGGTTACGGAAATACTTGT
GATGCCTA CCACATGACTTCTCCACATCCAGAAGGTCAGGGAGCTATCAAGGCCATCAAACTAGCCTTGGAAGAAGCTGA
GATTTCTC CAGAGCAAGTAGCCTATGTCAATGCTCACGGAACGTCAACTCCTGCCAATGAAAAAGGAGAAAGTGGTGCTA
TCGTAGCT

GTTCTTGGTAAGGAAGTACCTGTATCATCAACCAAGTCTTTTACAGGACATTTGCTGGGGCTGCGGGTGCA
GTAGAAGC

TATCGTCACCATCCAAGCTATGCGTCATAACTTTGTACCAATGACAGCTGGGACAAGTGAAGTATCAGATTA
TATCGAAG

CTAATGTCGTTTATGGACAAGGCTTGGAGAAAGAAATTCCATACGCTATTTCAAATACTTTTGGTTTTGGAG
GCCACAAT

GCAGTTCTTGCTTTCAAACGTTGGGAGAATAGATAA-3'
(B) *Streptococcus pneumoniae* fabF polypeptide sequence deduced from a [SEQ ID NO:2].
    polynucleotide sequence in this table
NH$_2$-
MKLNRVVVTGYGVTSPIGNTPEEFWNSLATGKIGIGGITKFDHSDFDVHNAAEIQDFPFDKYFVKKDTNRFD
NYSLYALY AAQEAVNHANLDVEALNRDRFGVIVASGIGGIKEIEDQVLRLHEKGPKRVKFMTLPKALFNMASGNVAMRFG
ANGVCKSI NTACSSSNDAIGDAFRSIKFGFQDVMLVGGTEASITPFAIAGFQALTALSTTEDPTRASIFFDKDRNGFVMG
EGSGMLVL ESLEHAEKRGATILAEVVGYGNTCDAYHMTSPHPEGQGAIKAIKLALEEAEISPEQVAYVNAHGTSTPANEK
GESGAIVA VLGKEVPVSSTKSFTGHLLGAAGAVEAIVTIEAMRHNFVFMTAGTSEVSDYIEANVVYGQGLEKEIFYAISN
TFGFGGHN
AVLAFKRWENR-COOH Deposited materials A deposit comprising a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on Apr. 11, 1996 and assigned deposit number 40794. The deposit was described as *Streptococcus pneumoniae* 0100993 on deposit.

On Apr. 17, 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain comprises a full length fabF gene. The sequence of the polynucleotides comprised in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited stain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule encoding a mature polypeptide expressible by the *Streptococcus pneumoniae* 0100993 strain, which polypeptide is comprised in the deposited strain. Further provided by the invention are fabF polynucleotide sequences in the deposited strain, such as DNA and RNA, and amino acid sequences encoded thereby. Also provided by the invention are fabF polypeptide and polynucleotide sequences isolated from the deposited strain.

Polypeptides fabF polypeptide of the invention is substantially phylogenetically related to other proteins of the fabF family.

In one aspect of the invention there are provided polypeptides of *Streptococcus pneumoniae* referred to herein as "fabF" and "fabF polypeptides" as well as biologically, diagnostically, prophylactically, clinically or therapeutically useful variants thereof, and compositions comprising the same.

Among the particularly preferred embodiments of the invention are variants of fabF polypeptide encoded by naturally occurring alleles of a fabF gene.

The present invention further provides for an isolated polypeptide that: (a) comprises or consists of an amino acid sequence that has at least 95% identity, most preferably at least 97–99% or exact identity, to that of SEQ ID NO:2 over the entire length of SEQ ID NO:2; (b) a polypeptide encoded by an isolated polynucleotide comprising or consisting of a polynucleotide sequence that has at least 95% identity, even more preferably at least 97–99% or exact identity to SEQ ID NO:1 over the entire length of SEQ ID NO:1; (c) a polypeptide encoded by an isolated polynucleotide comprising or consisting of a polynucleotide sequence encoding a polypeptide that has at least 95% identity, even more preferably at least 97–99% or exact identity, to the amino acid sequence of SEQ ID NO:2, over the entire length of SEQ ID NO:2.

The polypeptides of the invention include a polypeptide of Table 1 [SEQ ID NO:2] (in particular a mature polypeptide) as well as polypeptides and fragments, particularly those that has a biological activity of fabF, and also those that have at least 95% identity to a polypeptide of Table 1 [SEQ ID NO:2] and also include portions of such polypeptides with such portion of the polypeptide generally comprising at least 30 amino acids and more preferably at least 50 amino acids.

The invention also includes a polypeptide consisting of or comprising a polypeptide of the formula:

$$X\text{—}(R_1)_m\text{—}(R_2)\text{—}(R_3)_n\text{—}Y$$

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from *Streptococcus pneumoniae*, however, it may preferably be obtained from other organisms of the same taxonomic genus. A polypeptide of the invention may also be obtained, for example, from organisms of the same taxonomic family or order.

A fragment is a variant polypeptide having an amino acid sequence that is entirely the same as part but not all of any amino acid sequence of any polypeptide of the invention. As with fabF polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2], or of variants thereof, such as a continuous series of residues that includes an amino- and/or carboxyl-terminal amino acid sequence. Degradation forms of the polypeptides of the invention produced by or in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2, or an isolated polypeptide comprising an amino acid sequence having at least 15, 20, 30, 40, 50 or 100 contiguous amino acids truncated or deleted from the amino acid sequence of SEQ ID NO:2.

Fragments of the polypeptides of the invention may be employed for producing the corresponding full-length polypeptide by peptide synthesis; therefore, these variants may be employed as intermediates for producing the full-length polypeptides of the invention.

Polynucleotides

It is an object of the invention to provide polynucleotides that encode fabF polypeptides, particularly polynucleotides that encode a polypeptide herein designated fabF.

In a particularly preferred embodiment of the invention the polynucleotide comprises a region encoding fabF polypeptides comprising a sequence set out in Table 1 [SEQ ID NO:1] that includes a full length gene, or a variant thereof. This invention provides that this full length gene is essential to the growth and/or survival of an organism that possesses it, such as *Streptococcus pneumoniae.*

As a further aspect of the invention there are provided isolated nucleic acid molecules encoding and/or expressing fabF polypeptides and polynucleotides, particularly *Streptococcus pneumoniae* fabF polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a fabF polypeptide having a deduced amino acid sequence of Table 1 [SEQ ID NO:2] and polynucleotides closely related thereto and variants thereof.

In another particularly preferred embodiment of the invention there is a fabF polypeptide from *Streptococcus pneumoniae* comprising or consisting of an amino acid sequence of Table 1 [SEQ ID NO:2], or a variant thereof.

Using the information provided herein, such as a polynucleotide sequence set out in Table 1 [SEQ ID NO:1], a polynucleotide of the invention encoding fabF polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as a polynucleotide sequence given in Table 1 [SEQ ID NO:1], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in Table 1 [SEQ ID NO:1] was discovered in a DNA library derived from *Streptococcus pneumoniae* 0100993.

Moreover, each DNA sequence set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known to those skilled in the art. The polynucleotide of SEQ ID NO:1, between nucleotide number 1 and the stop codon that begins at nucleotide number 1234 of SEQ ID NO:1, encodes the polypeptide of SEQ ID NO:2.

In a further aspect, the present invention provides for an isolated polynucleotide comprising or consisting of: (a) a polynucleotide sequence that has at least 95% identity, even more preferably at least 97–99% or exact identity to SEQ ID NO:1 over the entire length of SEQ ID NO:1; (b) a polynucleotide sequence encoding a polypeptide that has at least 95% identity, even more preferably at least 97–99% or 100% exact, to the amino acid sequence of SEQ ID NO:2, over the entire length of SEQ ID NO:2.

A polynucleotide encoding a polypeptide of the present invention, including homologs and orthologs from species other than *Streptococcus pneumoniae,* may be obtained by a process that comprises the steps of screening an appropriate library under stringent hybridization conditions with a labeled or detectable probe consisting of or comprising the sequence of SEQ ID NO:1 or a fragment thereof; and isolating a full-length gene and/or genomic clones comprising said polynucleotide sequence.

The invention provides a polynucleotide sequence identical over its entire length to a coding sequence (open reading frame) in Table 1 [SEQ ID NO:1]. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also comprise at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of a fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of that may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide 1 to the nucleotide immediately upstream of or including nucleotide 1234 set forth in SEQ ID NO:1 of Table 1, both of that encode a fabF polypeptide.

The invention also includes a polynucleotide consisting of or comprising a polynucleotide of the formula:

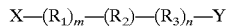

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, that can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Streptococcus pneumoniae,* however, it may preferably be obtained from other organisms of the same taxonomic genus. A polynucleotide of the invention may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* fabF having an amino acid sequence set out in Table 1 [SEQ ID NO:2]. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may comprise coding and/or non-coding sequences.

The invention further relates to variants of the polynucleotides described herein that encode variants of a polypeptide having a deduced amino acid sequence of Table 1 [SEQ ID NO:2]. Fragments of polynucleotides of the invention may be used, for example, to synthesize full-length polynucleotides of the invention.

Further particularly preferred embodiments are polynucleotides encoding fabF variants, that have the amino acid sequence of fabF polypeptide of Table 1 [SEQ ID NO:2] in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of fabF polypeptide.

Preferred isolated polynucleotide embodiments also include polynucleotides fragments, such as a polynucleotide comprising a nuclic acid sequence having at least 15, 20, 30, 40, 50 or 100 contiguous nucleic acids from the polynucleotide sequence of SEQ ID NO:1, or an polynucleotide comprising a nucleic acid sequence having at least 15, 20, 30, 40, 50 or 100 contiguous nucleic acids truncated or deleted from the 5' and/or 3' end of the polynucleotide sequence of SEQ ID NO:1.

Further preferred embodiments of the invention are polynucleotides that are at least 95% or 97% identical over their entire length to a polynucleotide encoding fabF polypeptide having an amino acid sequence set out in Table 1 [SEQ ID NO:2], and polynucleotides that are complementary to such polynucleotides. Most highly preferred are polynucleotides that comprise a region that is at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as a mature polypeptide encoded by a DNA of Table 1 [SEQ ID NO:1].

In accordance with certain preferred embodiments of this invention there are provided polynucleotides that hybridize, particularly under stringent conditions, to fabF polynucleotide sequences, such as those polynucleotides in Table 1.

The invention further relates to polynucleotides that hybridize to the polynucleotide sequences provided herein. In this regard, the invention especially relates to polynucleotides that hybridize under stringent conditions to the polynucleotides described herein. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library comprising a complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding fabF and to isolate cDNA and genomic clones of other genes that have a high identity, particularly high sequence identity, to a fabF gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have lee than 30 nucleotide residues or base pairs.

A coding region of a fabF gene may be isolated by screening using a DNA sequence provided in Table 1 [SEQ ID NO:1] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of Table 1 [SEQ ID NOS:1 or 2] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is a mature protein plus additional amino or carboxyl-terminal amino acids, or amino acids interior to a mature polypeptide (when a mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from a mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

As will be recognized, the entire polypeptide encoded by an open reading frame is often not required for activity. Accordingly, it has become routine in molecular biology to map the boundaries of the primary structure required for activity with N-terminal and C-terminal deletion experiments. These experiments utilize exonuclease digestion or convenient restriction sites to cleave coding nucleic acid sequence. For example, Promega (Madison, Wis.) sell an Erase-a-base™ system that uses Exonuclease, III designed to facilitate analysis of the deletion products (protocol available at www.promega.com). The digested endpoints can be repaired (e.g., by ligation to synthetic linkers) to the extent necessary to preserve an open reading frame. In this way, the nucleic acid of SEQ ID NO:1 readily provides contiguous fragments of SEQ ID NO:2 sufficient to provide an activity, such as an enzymatic, binding or antibody-inducing activity. Nucleic acid sequences encoding such fragments of SEQ ID NO:2 and variants thereof as described herein are within the invention, as are polypeptides so encoded.

As is known in the art, portions of the N-terminal and/or C-terminal sequence of a protein can generally be removed without serious consequence to the function of the protein. The amount of sequence that can be removed is often quite substantial. The nucleic acid cutting and deletion methods used for creating such deletion variants are now quite routine. Accordingly, any contiguous fragment of SEQ ID NO:2 which retains at least 20%, preferably at least 50%, of an activity of the polypeptide encoded by the gene for SEQ ID NO:2 is within the invention, as are corresponding fragment which are 70%, 80%, 90%, 95%,97%, 98% or 99% identical to such contiguous fragments. In one embodiment, the contiguous fragment comprises at least 70% of the amino acid residues of SEQ ID NO:2, preferably at least 80%, 90% or 95% of the residues.

In sum, a polynucleotide of the invention may encode a mature protein, a mature protein plus a leader sequence (that may be referred to as a preprotein), a precursor of a mature protein having one or more prosequences that are not the leader sequences of a preprotein, or a preproprotein, that is a precursor to a proprotein, having a leader sequence and one or more prosequences, that generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells that are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY,* (1986) and Sambrook, et al., *MOLECULAR CLONING: A LABORATORY MANUAL,* 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci E. coli, streptomyces, cyanobacteria, Bacillus subtilis, and Streptococcus pneumoniae; fungal cells, such as cells of a yeast, Kluveromyces, Saccharomyces, a basidiomycete, Candida albicans and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs may comprise control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of fabF polynucleotides and polypeptides of the invention for use as diagnostic reagents. Detection of fabF polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the fabF gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled fabF polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., Science, 230: 1242 (1985). Sequence changes at specific locations also may be revealed by nuclease protection assays, such as RNase, V1 and S1 protection assay or a chemical cleavage method. See, for example, Cotton et al., Proc. Natl. Acad. Sci., USA, 85: 4397–4401 (1985).

In another embodiment, an array of oligonucleotides probes comprising fabF nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., Science, 274: 610 (1996)).

Thus in another aspect, the present invention relates to a diagnostic kit that comprises: (a) a polynucleotide of the present invention, preferably the nucleotide sequence of SEQ ID NO:1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2. It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NO:1, that is associated with a disease or pathogenicity will provide a diagnostic tool that can add to, or define, a diagnosis of a disease, a prognosis of a course of disease, a determination of a stage of disease, or a susceptibility to a disease, that results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding fabF polypeptide can be used to identify and analyze mutations. The invention further provides these primers with 1, 2, 3 or 4 nucleotides removed from the 5' and/or the 3' end. These primers may be used for, among other things, amplifying fabF DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by Streptococcus pneumoniae, comprising determining from a sample derived from an individual, such as a bodily material, an increased level of expression of polynucleotide having a sequence of Table 1 [SEQ ID NO:1]. Increased or decreased expression of a fabF polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of fabF polypeptide compared to normal control tissue samples may be used to detect the presence of an infection, for example. Assay techniques that can be used to determine levels of a fabF polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Polypeptides and polynucleotides of the present invention are responsible for many biological functions, including many disease states, in particular the Diseases herein mentioned. It is therefore desirable to devise screening methods to identify compounds that agonize (e.g., stimulate) or that antagonize (e.g., inhibit) the function of the polypeptide or polynucleotide. Accordingly, in a further aspect, the present invention provides for a method of screening compounds to identify those that agonize or that antagonize the function of a polypeptide or polynucleotide of the invention, as well as related polypeptides and polynucleotides. In general, agonists or antagonists (e.g., inhibitors) may be employed for therapeutic and prophylactic purposes for such Diseases as herein mentioned. Compounds may be identified from a variety of sources, for example, cells, cell-free preparations, chemical libraries, and natural product mixtures. Such agonists and antagonists so-identified may be natural or modified substrates, ligands, receptors, enzymes, etc., as the case may be, of fabF polypeptides and polynucleotides; or may be structural or functional mimetics thereof (see Coligan et al., *Current Protocols in Immunology* 1(2):Chapter 5 (1991)).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists, in the absence of an agonist or antagonist, by testing whether the candidate compound results in inhibition of activation of the polypeptide or polynucleotide, as the case may be. Further, the screening methods may simply comprise the steps of mixing a candidate compound with a solution comprising a polypeptide or polynucleotide of the present invention, to form a mixture, measuring fabF polypeptide and/or polynucleotide activity in the mixture, and comparing the fabF polypeptide and/or polynucleotide activity of the mixture to a standard. Fusion proteins, such as those made from Fc portion and fabF polypeptide, as herein described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

The invention also provides a method of screening compounds to identify those that enhance (agonist) or block (antagonist) the action of fabF polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising fabF polypeptide and a labeled substrate or ligand of such polypeptide is incubated in the absence or the presence of a candidate molecule that may be a fabF agonist or antagonist. The ability of the candidate molecule to agonize or antagonize the fabF polypeptide is reflected in decreased binding of the labeled ligand or decreased production of product from such substrate. Molecules that bind gratuitously, i.e., without inducing the effects of fabF polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to calorimetric, labeled substrate converted into product, a reporter gene that is responsive to changes in fabF polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide that compete with the binding of the polypeptide to its receptor(s), if any. Standard methods for conducting such assays are well understood in the art.

The fluorescence polarization value for a fluorescently-tagged molecule depends on the rotational correlation time or tumbling rate. Protein complexes, such as formed by fabF polypeptide associating with another fabF polypeptide or other polypeptide, labeled to comprise a fluorescently-labeled molecule will have higher polarization values than a fluorescently labeled monomeric protein. It is preferred that this method be used to characterize small molecules that disrupt polypeptide complexes.

Fluorescence energy transfer may also be used characterize small molecules that interfere with the formation of fabF polypeptide dimers, trimers, tetramers or higher order structures, or structures formed by fabF polypeptide bound to another polypeptide. fabF polypeptide can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of small molecules on fabF polypeptide self-association as well as an association of fabF polypeptide and another polypeptide or small molecule. fabF polypeptide can be coupled to a sensor chip at low site density such that covalently bound molecules will be monomeric. Solution protein can then passed over the fabF polypeptide-coated surface and specific binding can be detected in real-time by monitoring the change in resonance angle caused by a change in local refractive index. This technique can be used to characterize the effect of small molecules on kinetic rates and equilibrium binding constants for fabF polypeptide self-association as well as an association of fabF polypeptide and another polypeptide or small molecule.

A scintillation proximity assay may be used to characterize the interaction between an association of fabF polypeptide with another fabF polypeptide or a different polypeptide. fabF polypeptide can be coupled to a scintillation-filled bead. Addition of radio-labeled fabF polypeptide results in binding where the radioactive source molecule is in close proximity to the scintillation fluid. Thus, signal is emitted upon fabF polypeptide binding and compounds that prevent fabF polypeptide self-association or an association of fabF polypeptide and another polypeptide or small molecule will diminish signal.

In other embodiments of the invention there are provided methods for identifying compounds that bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for fabF agonists is a competitive assay that combines fabF and a potential agonist with fabF-binding molecules, recombinant fabF binding molecules, natural substrates or ligands, or substrate or ligand mimetics, under appropriate conditions for a competitive inhibition assay. fabF can be labeled, such as by radioactivity or a colorimetric compound, such that the number of fabF molecules bound to a binding molecule or converted to product can be determined accurately to assess the effectiveness of the potential antagonist.

It will be readily appreciated by the skilled artisan that a polypeptide and/or polynucleotide of the present invention may also be used in a method for the structure-based design of an agonist or antagonist of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist or antagonist; (c) synthesizing candidate compounds that are predicted to bind to or react with the deduced binding site(s), reactive site(s), and/or motif(s); and (d) testing whether the candidate compounds are indeed agonists or antagonists. It will be further appreciated that this will normally be an iterative process, and this iterative process may be performed using automated and computer-controlled steps.

In a further aspect, the present invention provides methods of treating abnormal conditions such as, for instance, a Disease, related to either an excess of, an under-expression of, an elevated activity of, or a decreased activity of fabF polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the fabF polypeptide and/or polypeptide.

In still another approach, expression of the gene encoding endogenous fabF polypeptide can be inhibited using expression blocking techniques. This blocking may be targeted against any step in gene expression, but is preferably targeted against transcription and/or translation. An examples of a known technique of this sort involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides that form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial fabF proteins that mediate tissue damage and/or; to block the normal progression of pathogenesis in infections initiated other than by the implantation of in-dwelling devices or by other surgical techniques.

In accordance with yet another aspect of the invention, there are provided fabF agonists and antagonists, preferably bacteristatic or bactericidal agonists and antagonists.

The antagonists and agonists of the invention may be employed, for instance, to prevent, inhibit and/or treat diseases.

Antagonists of the invention include, among others, small organic molecules, peptides, polypeptides and antibodies that bind to a polynucleotide and/or polypeptide of the invention and thereby inhibit or extinguish its activity or expression. Antagonists also may be small organic molecules, a peptide, a polypeptide such as a closely related protein or antibody that binds the same sites on a binding molecule, such as a binding molecule, without inducing fabF-induced activities, thereby preventing the action or expression of fabF polypeptides and/or polynucleotides by excluding fabF polypeptides and/or polynucleotides from binding.

Antagonists of the invention also include a small molecule that binds to and occupies the binding site of the polypeptide thereby preventing binding to cellular binding molecules, such that normal. biological activity is prevented. Examples of small molecules include but are not limited to small organic molecules, peptides or peptide-like molecules. Other antagonists include antisense molecules (see Okano, *J. Neurochem.* 56: 560 (1991); OLIGODEOXYNUCLEOTIDES AS ANTISENSE INHIBITORS OF GENE EXPRESSION, CRC Press, Boca Raton, Fla. (1988), for a description of these molecules). Preferred antagonists include compounds related to and variants of fabF.

Other examples of polypeptide antagonists include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or small molecules that bind to the polypeptide of the present invention but do not elicit a response, so that the activity of the polypeptide is prevented.

Small molecules of the invention preferably have a molecular weight below 2,000 daltons, more preferably between 300 and 1,000 daltons, and most preferably between 400 and 700 daltons. It is preferred that these small molecules are organic molecules.

*Helicobacter pylori* (herein "*H. pylori*") bacteria infect the stomachs of over one-third of the world's population causing stomach cancer, ulcers, and gastritis (International Agency for Research on Cancer (1994) *Schistosomes, Liver Flukes and Helicobacter Pylori* (International Agency for Research on Cancer, Lyon, France, http://www.uicc.ch/ecp/ecp2904.htm). Moreover, the International Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of fabF polypeptides and/or polynucleotides) found using screens provided by the invention, or known in the art, particularly narrow-spectrum antibiotics, should be useful in the treatment of *H. pylori* infection. Such treatment should decrease the advent of *H. pylori*-induced cancers, such as gastrointestinal carcinoma. Such treatment should also prevent, inhibit and/or cure gastric ulcers and gastritis.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Glossary

The following definitions are provided to facilitate understanding of certain terms used frequently herein.

"Bodily material(s)" means any material derived from an individual or from an organism infecting, infesting or inhabiting an individual, including but not limited to, cells, tissues and waste, such as, bone, blood, serum, cerebrospinal fluid, semen saliva, muscle, cartilage, organ tissue, skin, urine, stool or autopsy materials.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid.

"Host cell(s)" is a cell that has been introduced (e.g., transformed or transfected) or is capable of introduction (e.g., transformation or transfection) by an exogenous polynucleotide sequence.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y)$$

wherein $n_n$ is the number of nucleotide alterations, $x_n$ is the total number of nucleotides in SEQ ID NO:1, y is 0.95 for 95%, 0.97 for 97% or 1.00 for 100%, and · is the symbol for the multiplication operator, and wherein any non-integer product of xn and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y)$$

wherein $n_a$ is the number of amino acid alterations, $x_a$ is the total number of amino acids in SEQ ID NO:2, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Individual(s)" means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi,* Bordetella, *Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis,* (ii) an archaeon, including but not limited to Archaebacter, and (ii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis,* or *Candida albicans.*

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR*

PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, that are well known and routine to those of skill in the art, except where otherwise described in detail. The examples are illustrative, but do not limit the invention.

Example 1

Strain Selection, Library Production and Sequencing

The polynucleotide having a DNA sequence given in Table 1 [SEQ ID NO:1] was obtained from a library of clones of chromosomal DNA of *Streptococcus pneumoniae* in *E. coli*. The sequencing data from two or more clones comprising overlapping *Streptococcus pneumoniae* DNAs was used to construct the contiguous DNA sequence in SEQ ID NO:1. Libraries may be prepared by routine methods, for example: Methods 1 and 2 below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2 fabF Characterization

Gene expression in vivo

Recently several novel approaches have been described which purport to follow global gene expression during infection (Chuang, S. et al., (1993); Mahan, M. J. et al., Science 259:686–688 (1993); Hensel, M. et al., Science 269:400–403 (1995). These new techniques have so far been demonstrated with gram negative pathogen infections but not with infections with gram positives presumably because the much slower development of global transposon mutagenesis and suitable vectors needed for these strategies in these organisms, and in the case of that process described by Chuang, S. et al., J. Bacteriol. 175:2026–2036 (1993) the difficulty of isolating suitable quantities of bacterial RNA free of mammalian RNA derived from the infected tissue to furnish bacterial RNA labelled to sufficiently high specific activity.

The present invention employs a novel technology to determine gene expression in the pathogen at different stages of infection of the mammalian host. A novel aspect of this invention is the use of a suitably labelled oligonucleotide probe which anneals specifically to the bacterial ribosomal RNA in Northern blots of bacterial RNA preparations from infected tissue. Using the more abundant ribosomal RNA as a hybridization target greatly facilitates the optimisation of a protocol to purify bacterial RNA of a suitable size and quantity for RT-PCR from infected tissue.

A suitable oligonucleotide useful for applying this method to genes expressed in *Staphylococcus aureus* is 5'-gctcctaaaaggttactccaccggc-3' [SEQ ID NO:3].

Use of the technology of the present invention enables identification of bacterial genes transcribed during infection, inhibitors of which would have utility in anti-bacterial therapy. Specific inhibitors of such gene transcription or of the subsequent translation of the resultant mRNA or of the function of the corresponding expressed proteins would have utility in anti-bacterial therapy.

The determination of expression during infection of the fabF gene from *Streptococcus pneumoniae*

Necrotic fatty tissue from a four day groin infection of Streptococcus pneumoniae 0100993 in the mouse is efficiently disrupted and processed in the presence of chaotropic agents and RNAase inhibitor to provide a mixture of animal and bacterial RNA. The optimal conditions for disruption and processing to give stable preparations and high yields of bacterial RNA are followed by the use of hybridisation to a radiolabelled oligonucleotide specific to *Streptococcus pneumoniae* 16S RNA on Northern blots. The RNAase free, DNAase free, DNA and protein free preparations of RNA obtained are suitable for Reverse Transcription PCR (RT-PCR) using unique primer pairs designed from the sequence of each gene of *Streptococcus pneumoniae* 0100993.

a) Isolation of tissue infected with *Streptococcus pneumoniae* 0100993 from a mouse animal model of infection 10 ml. volumes of sterile nutrient broth (No. 2 Oxoid) are seeded with isolated, individual colonies of *Streptococcus pneumoniae* 0100993 from an agar culture plate. The cultures are incubated aerobically (static culture) at 37° C. for 16–20 hours. 4 week old mice (female,18 g–22 g, strain MF1) are each infected by subcutaneous injection of 0.5 ml. of this broth culture of *Streptococcus pneumoniae* 0100993 (diluted in broth to approximately $10^8$ cfu/ml.) into the anterior, right lower quadrant (groin area). Mice should be monitored regularly during the first 24 hours after infection, then daily until termination of study. Animals with signs of systemic infection, i.e. lethargy, ruffled appearance, isolation from group, should be monitored closely and if signs progress to moribundancy, the animal should be culled immediately.

Visible external signs of lesion development will be seen 24–48 h after infection. Examination of the abdomen of the animal will show the raised outline of the abscess beneath the skin. The localised lesion should remain in the right lower quadrant, but may occasionally spread to the left lower quadrant, and superiorly to the thorax. On occasions, the abscess may rupture through the overlying skin layers. In such cases the affected animal should be culled immediately and the tissues sampled if possible. Failure to cull the animal may result in the necrotic skin tissue overlying the abscess being sloughed off, exposing the abdominal muscle wall.

Approximately 96 hours after infection, animals are killed using carbon dioxide asphyxiation. To minimise delay between death and tissue processing /storage, mice should be killed individually rather than in groups. The dead animal is placed onto its back and the fur swabbed liberally with 70% alcohol. An initial incision using scissors is made through the skin of the abdominal left lower quadrant, travelling superiorly up to, then across the thorax. The incision is completed by cutting inferiorly to the abdominal lower right quadrant. Care should be taken not to penetrate the abdominal wall. Holding the skin flap with forceps, the skin is gently pulled way from the abdomen. The exposed abscess, which covers the peritoneal wall but generally does not penetrate the muscle sheet completely, is excised, taking care not to puncture the viscera The abscess/muscle sheet and other infected tissue may require cutting in sections, prior to flash-freezing in liquid nitrogen, thereby allowing easier storage in plastic collecting vials.

b) Isolation of *Streptococcus pneumoniae* 0100993 RNA from infected tissue samples 4–6 infected tissue samples (each approx 0.5–0.7 g) in 2 ml screw-cap tubes are removed from −80° C. storage into a dry ice ethanol bath In a microbiological safety cabinet the samples are disrupted individually whilst the remaining samples are kept cold in the dry ice ethanol bath. To disrupt the bacteria within the tissue sample 1 ml of TRIzol Reagent (Gibco BRL, Life Technologies) is added followed by enough 0.1 mm zirconia/silica beads to almost fill the tube, the lid is replaced taking care not to get any beads into the screw thread so as to ensure a good seal and eliminate aerosol generation. The sample is then homogenised in a Mini-BeadBeater Type BX-4 (Biospec Products). Necrotic fatty tissue isstrain treated for 100 seconds at 5000 rpm in order to achieve bacterial lysis. In vivo grown bacteria require longer treatment than in vitro grown *Streptococcus pneumoniae* Streptococcus which are disrupted by a 30 second bead-beat.

After bead-beating the tubes are chilled on ice before opening in a fume-hood as heat generated during disruption may degrade the TRIzol and release cyanide.

200 microliters of chloroform is then added and the tubes shaken by hand for 15 seconds to ensure complete mixing. After 2–3 minutes at room temperature the tubes are spun down at 12,000×g, 4° C. for 15minutes and RNA extraction is then continued according to the method given by the manufacturers of TRIzol Reagent i.e.:—The aqueous phase, approx 0.6 ml, is transferred to a sterile eppendorf tube and 0.5 ml of isopropanol is added. After 10 minutes at room temperature the samples are spun at 12,000×g, 4° C. for 10 minutes. The supernatant is removed and discarded then the RNA pellet is washed with 1 ml 75% ethanol. A brief vortex is used to mix the sample before centrifuging at 7,500×g, 4° C. for 5 minutes. The ethanol is removed and the RNA pellet dried under vacuum for no more than 5 minutes. Samples are then resuspended by repeated pipetting in 100 microliters of DEPC treated water, followed by 5–10 minutes at 55° C. Finally, after at least 1 minute on ice, 200 units of Rnasin (Promega) is added.

RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels stained with ethidium bromide are used to visualise total RNA yields. To demonstrate the isolation of bacterial RNA from the infected tissue 1×MOPS, 2.2M formaldehyde gels are run and vacuum blotted to Hybond-N (Amersham). The blot is then hybridised with a $^{32}$P labelled oligonucletide probe specific to 16s rRNA of *Streptococcus pneumoniae* (K. Greisen, M. Loeffelholz, A. Purohit and D. Leong. J. Clin. (1994) Microbiol. 32 335–351 ). The oligonucleotide of the sequence is used as a probe. The size of the hybridising band is compared to that of control RNA isolated from in vitro grown *Streptococcus pneumoniae* 0100993 in the Northern blot. Correct sized bacterial 16s rRNA bands can be detected in total RNA samples which show extensive degradation of the mammalian RNA when visualised on TBE gels.

c) The removal of DNA from *Streptococcus pneumoniae* 0100993-derived RNA

DNA was removed from 73 microliter samples of RNA by a 15 minute treatment on ice with 3 units of DNAaseI, amplification grade (Gibco BRL, Life Technologies) in the buffer supplied with the addition of 200 units of Rnasin (Promega) in a final volume of 90 microliters.

The DNAase was inactivated and removed by treatment with TRIzol LS Reagent (Gibco BRL, Life Technologies) according to the manufacturers protocol.

DNAase treated RNA was resuspended in 73 microliters of DEPC treated water with the addition of Rnasin as described in Method 1.

d) The preparation of cDNA from RNA samples derived from infected tissue 10 microliter samples of DNAase treated RNA are reverse transcribed using a SuperScript Preamplification System for First Strand cDNA Synthesis kit (Gibco BRL, Life Technologies) according to the manufacturers instructions. 1 nanogram of random hexamers is used to prime each reaction. Controls without the addition of SuperScriptII reverse transcriptase are also run. Both +/−RT samples are treated with RNaseH before proceeding to the PCR reaction e) The use of PCR to determine the presence of a bacterial cDNA species PCR reactions are set up on ice in 0.2 ml tubes by adding the following components: 45 microliters PCR SUPERMIX (Gibco BRL, Life Technologies); 1 microliter 50 mM $MgCl_2$, to adjust final concentration to 2.5 mM; 1 microliter PCR primers(optimally 18–25 basepairs in length and designed to possess similar annealing temperatures), each primer at 10 mM initial concentration; and 2 microliters cDNA.

PCR reactions are run on a Perkin Elmer GeneAmp PCR System 9600 as follows: 5 minutes at 95° C., then 50 cycles of 30 seconds each at 94° C., 42° C. and 72° C. followed by 3 minutes at 72° C. and then a hold temperature of 4° C. (the number of cycles is optimally 30–50 to determine the appearance or lack of a PCR product and optimally 8–30 cycles if an estimation of the starting quantity of cDNA from the RT reaction is to be made); 10 microliter aliquots are then run out on 1% 1×TBE gels stained with ethidium bromide with PCR product, if present, sizes estimated by comparison to a 100 bp DNA Ladder (Gibco BRL, Life Technologies). Alternatively if the PCR products are conveniently labelled by the use of a labelled PCR primer (e.g. labelled at the 5' end with a dye) a suitable aliquot of the PCR product is run out on a polyacrylamide sequencing gel and its presence and quantity detected using a suitable gel scanning system (e.g. ABI Prism™ 377 Sequencer using GeneScan™ software as supplied by Perkin Elmer).

RT/PCR controls may include +/− reverse transcriptase reactions, 16s rRNA primers or DNA specific primer pairs designed to produce PCR products from non-transcribed *Streptococcus pneumoniae* 0100993 genomic sequences.

To test the efficiency of the primer pairs they are used in DNA PCR with *Streptococcus pneumoniae* 0100993 total DNA. PCR reactions are set up and run as described above using approx. 1 microgram of DNA in place of the cDNA and 35 cycles of PCR.

Primer pairs which fail to give the predicted sized product in either DNA PCR or RT/PCR are PCR failures and as such are uninformative. Of those which give the correct size product with DNA PCR two classes are distinguished in RT/PCR: 1. Genes which are not transcribed in vivo reproducibly fail to give a product in RT/PCR; and 2. Genes which are transcribed in vivo reproducibly give the correct size product in RT/PCR and show a stronger signal in the +RT samples than the signal (if at all present) in −RT controls.

Two polynucleotide sequences of the invention, SEQ ID NOS:1 and 3, were identified in the above test as transcribed in vivo. SEQ ID NO:2 was deduced from the polynucleotide sequence given as SEQ ID NO:1. SEQ ID NO:4 was deduced from the polynucleotide sequence given as SEQ ID NO:3. The pair of PCR primers used to identify the gene are given as SEQ ID NOS:5 and 6.

Using this technique, the *S. pneumoniae* fabF transcript was shown to be present in vivo in the 12 hour and 48 hour RTI model at moderate levels. Similar transcript levels were seen in vitro from log-phase growth in rich media.

The determination of essentiality of the fabF gene from *Streptococcus pneumoniae*

An allelic replacement cassette is generated using PCR technology. The cassette typically consists of a pair of 500 bp chromosomal DNA fragments flanking an erythromycin resistance gene. The chromosomal DNA sequences are usually the 500 bp preceding and following the gene of interest.

Attempts are made to introduce the allelic replacement cassette into *S. pneumoniae* R6 or *S. pneumoniae* 100993 by transformation. Competent cells are prepared according to published protocols. DNA is introduced into the cells by incubation of 500 ng of allelic replacement cassette with $10^6$ cells at 30° C. for 30 minutes. The cells are transferred to 37° C. for 90 minutes to allow expression of the erythromycin resistance gene. Cells are plated in agar containing 1ug erythromycin per ml. Following incubation at 37° C. for 36 hours, any observed colonies are picked and grown overnight in Todd-Hewitt broth supplemented with 0.5% yeast extract. Typically, in positive control experiments carried out in parallel which target a non-essential gene, $10^2$–$10^3$ transformants containing the appropriate allelic replacement are obtained. If erythromycin resistant colonies are only observed in transformation experiments using *S. pneumoniae* R6, DNA from these cells are used to transform *S. pneumoniae* 100993. The transformation procedure is identical to that for *S. pneumoniae* R6 except that a competence stimulating heptadecapeptide (Havarstein et al., (1995) P.N.A.S. 92, 11140–11144) is added at a concentration of 1 ug/ml in the initial transformation mix. Mutants are selected by their ability to grow in agar containing 1 ug erythromycin per ml.

If no transformants are obtained in three separate transformation experiments, then the target gene is considered as being essential in vitro.

However, if colonies are obtained chromosomal DNA is prepared from these cells and examined using diagnostic PCR. Oligonucleotides designed to hybridize to sequences within the allelic replacement cassette are used in conjunction with DNA primers hybridizing to chromosomal sequences outside the cassette to generate DNA products amplified by PCR of characteristic size. This chromosomal DNA is also subject to Southern analysis in order to verify that the appropriate chromosomal DNA rearrangement has occurred.

In order to demonstrate that the mutation is stably maintained, the defective strain is grown for many generations in the absence of selective pressure and then assayed for its ability to grow in the absence and presence of erythromycin.

The *S. pneumoniae* fabF gene could not be knocked out using this technology, so it was concluded that this gene is essential for growth in vitro.

The Cloning, Expression and Purification of *S. pneumoniae* FabF Protein

In order to provide FabF protein for enzymatic assay, the fabF gene was cloned from *S. pneumoniae* and overexpressed in *E. coli*.

The fabF gene was PCRed from *S. pneumoniae* 0100993 genomic DNA and cloned into the pET28a(+) vector (Novagen) between the NdeI and EcoRI restriction enzyme sites, to provide an open reading frame (shown below) consisting of a hexa-His tag, a thrombin protease cleavage site, followed by the fabF gene, all under the control of the T7lac promoter.

>S. pneumoniae His6-tagged FabF [SEQ ID NO:4]
MGSSHHHHHHSSGLVPRGSHMKLNRVVVTGYGVTSPIGNTPEEFWNSLATGKIGIGGITKFDHSDFDVHNAA
EIQDFPFD KYFVKKDTNRFDNYSLYALYAAQEAVNHANLDVEALNRDRFGVIVASGIGGIKEIEDQVLRLHEKGPKRVKP
MTLPKALP NMASGNVAMRFGANGVCKSINTACSSSNDAIGDAFRSIKFGFQDVMLVGGTEASITPFAIAGFQALTALSTT
EDPTRASI PFDKDRNGFVMGEGSGMLVLESLEHAEKRGATILAEVVGYGNTCDAYHMTSPHPEGQGAIKAIKLALEEAEI
SPEQVAYV NAHGTSTPANEKGESGAIVAVLGKEVPVSSTKSFTGHLLGAAGAVEAIVTIEAMRHNFVPMTAGTSEVSDYI
EANVVYGQ

GLEKEIPYAISNTFGFGGHNAVLAFKRWENR

The resulting plasmid construct, called pET-FabF, was transformed into *E. coli* strain BL21(DE3) and selected on LB media containing 1% glucose and 50 ug/ml Kanamycin. A single colony was inoculated into 5 ml of LB media containing 1% glucose and 50 ug/ml Kanamycin, and grown overnight at 37° C. with shaking. This culture was seeded into 500 ml of fresh LB media containing 1% glucose and 50 ug/ml Kanamycin and grown at 37° C. with shaking, to mid-log phase (OD at 600 nm=0.6). Expression of the hexaHis-tagged FabF was induced by adding IPTG to 1 mM and, continuing growth for 3 hours at 37° C. under the same conditions. The cells were pelleted and resuspended in 5 ml lysis buffer per gram wet weight of cells (lysis buffer=10 mM imidazole, 50 mM phosphate buffer, 0.5M NaCl, 5 mM beta-mercaptoethanol pH7.5). Lysozyme was added to 0.1 mg/ml and the sample incubated on ice for 30 minutes. Four cycles of sonication, freeze/thaw were done and the lysate was clarified by centrifugation and applied to a 1 ml room temperature HiTrap chelating column (Amersham Pharmacia) charged with $NiSO_4$. After washing with lysis buffer, the protein was eluted with lysis buffer containing 100 mM and 500 mM imidazole and exchanged into 50 mM Tris pH7.5, 0.2M NaCl and 2 mM DTT using PD-10 desalting columns, and then dialyzed overnight at 4° C. against 2L of the same buffer. This yielded 30mg of 90% pure hexa-His-tagged FabF.

fabF Characterization

A. Measurement of β-ketoacyl-ACP synthase (FabF) activity

The enzyme catalyses condensation of acyl-ACP with malonyl-ACP to form the corresponding β-ketoacyl-ACP and can be assayed in several ways:

(1) The ability of FabF to function in the initial cycle of fatty acid synthesis can be determined in assays containing a combination of the enzymes encompassing the complete Gram-positive bacterial fatty acid biosynthetic pathway (FabD, H, G, Z, I and F).

For example, a reaction comprising FabD, FabH, FabG, FabZ and FabI enzymes, ACP, NADH, and NADPH cofactors, and acetyl-CoA and [2-$^{14}$C]-malonyl-CoA substrates can be used to produce [$^{14}$C]butyryl-ACP in situ. FabF activity can be assayed following addition of FabF and incubation. Reaction progress can be assayed following separation and quantification of reaction products using techniques such as conformationally sensitive gel electrophoresis or mass spectroscopy. Alternatively, an excess of biotinylated malonyl-ACP could be added to the reaction at the same time as FabF and the subsequently formed radio-active biotinylated β-ketoacyl-ACP can be assayed using Scintillation Proximity Assay techniques.

Alternatively, FabF can be assayed independently using substrate prepared by biotransformation using the above reagents, followed by purification of the [$^{14}$C]-butyryl-ACP. Alternative longer chain (to 16 carbon length) radiolabeled acyl-ACPs may be prepared similarly, and substituted. FabF reaction progress or inhibition can be assayed as described above after addition of malonyl-ACP or biotinylated malony-ACP and incubation with isolated susbtrate. Radioactive β-ketoacyl-ACP can be precipitated with TCA and quantitated by scintillation counting, or radioactive biotinylated β-ketoacyl-ACP production can be assayed using Scintillation Proximity Assay techniques.

Ligand binding to FabF

It is also possible to define ligand interactions with FabF in experiments that are not dependent upon enzyme catalyzed turnover of substrates. This type of experiment can be done in a number of ways:

(1) Effects of ligand binding upon enzyme intrinsic fluorescence (e.g. of tryptophan)

Binding of either natural ligands or inhibitors may result in enzyme conformational changes which alter enzyme fluorescence. Using stopped-flow fluorescence equipment, this can be used to define the microscopic rate constants that describe binding. Alternatively, steady-state fluorescence titration methods can yield the overall dissociation constant for binding in the same way that these are accessed through enzyme inhibition experiments.

(2) Spectral effects of ligands

Where the ligands themselves are either fluorescent or possess chromophores that overlap with enzyme tryptophan fluorescence, binding can be detected either via changes in the ligand fluorescence properties (e.g. intensity, lifetime or polarization) or fluorescence resonance energy transfer with enzyme tryptophans. The ligands could either be inhibitors or variants of the natural ligands.

(3) Thermal analysis of the enzyme:ligand complex

Using calorimetric techniques (e.g. Isothermal Calorimetry, Differential Scanning Calorimetry) it is possible to detect thermal changes, or shifts in the stability of FabF which reports and therefore allows the characterization of ligand binding.

What is claimed is:

1. An isolated polypeptide comprising the amino acid sequence set forth in SEQ ID NO:2.

2. A composition comprising the isolated polypeptide of claim 1 and a pharmaceutically acceptable carrier.

3. A fusion polypeptide comprising a heterologous amino acid sequence fused to the isolated polypeptide of claim 1.

4. A composition comprising the fusion polypeptide of claim 3 and a pharmaceutically acceptable carrier.

5. The isolated polypeptide of claim 1, wherein the isolated polypeptide consists of amino acid sequence set forth in SEQ ID NO:2.

6. A composition comprising the isolated polypeptide of claim 5 and a pharmaceutically acceptable carrier.

* * * * *

SEQUENCE LISTING

<160> NUMBER OF SEQ ID NOS: 4

<210> SEQ ID NO 1
<211> LENGTH: 1236
<212> TYPE: DNA
<213> ORGANISM: Streptococcus pneumoniae

<400> SEQUENCE: 1

| | | | | | |
|---|---|---|---|---|---|
| atgaaactaa | atcgagtagt | ggtaacaggt | tatggagtaa | catctccaat cggaaataca | 60 |
| ccagaagaat | tttggaatag | tttagcaact | gggaaaatcg | gcattggtgg cattacaaaa | 120 |
| tttgatcata | gtgactttga | tgtgcataat | gcggcagaaa | tccaagattt tccgttcgat | 180 |
| aaatactttg | taaaaaaga | taccaaccgt | tttgataact | attctttata tgccttgtat | 240 |
| gcagcccaag | aggctgtaaa | tcatgccaat | cttgatgtag | aggctcttaa tagggatcgt | 300 |
| tttggtgtta | tcgttgcatc | tggtattggt | ggaatcaagg | aaattgaaga tcaggtactt | 360 |
| cgccttcatg | aaaaggacc | caaacgtgtc | aaaccaatga | ctcttccaaa agctttacca | 420 |
| aatatggctt | ctgggaatgt | agccatgcgt | tttggtgcaa | acggtgtttg taaatctatc | 480 |
| aatactgcct | gctcttcatc | aaatgatgcg | attggggatg | ccttccgctc cattaagttt | 540 |
| ggtttccaag | atgtgatgtt | ggtgggagga | acagaagctt | ctatcacacc ttttgccatc | 600 |
| gctggtttcc | aagccttaac | agctctctct | actacagagg | atccaactcg tgcttcgatc | 660 |
| ccatttgata | aggatcgcaa | tgggtttgtt | atgggtgaag | gttcagggat gttggttcta | 720 |
| gaaagtcttg | aacacgctga | aaaacgtgga | gctactatcc | tggctgaagt ggttggttac | 780 |
| ggaaatactt | gtgatgccta | ccacatgact | tctccacatc | cagaaggtca gggagctatc | 840 |
| aaggccatca | aactagcctt | ggaagaagct | gagatttctc | cagagcaagt agcctatgtc | 900 |
| aatgctcacg | gaacgtcaac | tcctgccaat | gaaaaaggag | aaagtggtgc tatcgtagct | 960 |
| gttcttggta | aggaagtacc | tgtatcatca | accaagtctt | ttacaggaca tttgctgggg | 1020 |
| gctgcgggtg | cagtagaagc | tatcgtcacc | atcgaagcta | tgcgtcataa cttttgtacca | 1080 |
| atgacagctg | gacaagtga | agtatcagat | tatatcgaag | ctaatgtcgt ttatggacaa | 1140 |
| ggcttggaga | aagaaattcc | atacgctatt | tcaaatactt | ttggttttgg aggccacaat | 1200 |
| gcagttcttg | ctttcaaacg | ttgggagaat | agataa | | 1236 |

<210> SEQ ID NO 2
<211> LENGTH: 411
<212> TYPE: PRT
<213> ORGANISM: Streptococcus pneumoniae

<400> SEQUENCE: 2

Met Lys Leu Asn Arg Val Val Thr Gly Tyr Gly Val Thr Ser Pro
 1               5                  10                  15

Ile Gly Asn Thr Pro Glu Glu Phe Trp Asn Ser Leu Ala Thr Gly Lys
                20                  25                  30

Ile Gly Ile Gly Gly Ile Thr Lys Phe Asp His Ser Asp Phe Asp Val
            35                  40                  45

His Asn Ala Ala Glu Ile Gln Asp Phe Pro Asp Lys Tyr Phe Val
        50                  55                  60

Lys Lys Asp Thr Asn Arg Phe Asp Asn Tyr Ser Leu Tyr Ala Leu Tyr
65                  70                  75                  80

Ala Ala Gln Glu Ala Val Asn His Ala Asn Leu Asp Val Glu Ala Leu
                85                  90                  95

Asn Arg Asp Arg Phe Gly Val Ile Val Ala Ser Gly Ile Gly Ile
            100                 105                 110

Lys Glu Ile Glu Asp Gln Val Leu Arg Leu His Glu Lys Gly Pro Lys
            115                 120                 125

Arg Val Lys Pro Met Thr Leu Pro Lys Ala Leu Pro Asn Met Ala Ser
130                 135                 140

Gly Asn Val Ala Met Arg Phe Gly Ala Asn Gly Val Cys Lys Ser Ile
145                 150                 155                 160

Asn Thr Ala Cys Ser Ser Asn Asp Ala Ile Gly Asp Ala Phe Arg
            165                 170                 175

Ser Ile Lys Phe Gly Phe Gln Asp Val Met Leu Val Gly Thr Glu
            180                 185                 190

Ala Ser Ile Thr Pro Phe Ala Ile Ala Gly Phe Gln Ala Leu Thr Ala
            195                 200                 205

Leu Ser Thr Thr Glu Asp Pro Thr Arg Ala Ser Ile Pro Phe Asp Lys
210                 215                 220

Asp Arg Asn Gly Phe Val Met Gly Glu Gly Ser Gly Met Leu Val Leu
225                 230                 235                 240

Glu Ser Leu Glu His Ala Glu Lys Arg Gly Ala Thr Ile Leu Ala Glu
            245                 250                 255

Val Val Gly Tyr Gly Asn Thr Cys Asp Ala Tyr His Met Thr Ser Pro
            260                 265                 270

His Pro Glu Gly Gln Gly Ala Ile Lys Ala Ile Lys Leu Ala Leu Glu
            275                 280                 285

Glu Ala Glu Ile Ser Pro Glu Gln Val Ala Tyr Val Asn Ala His Gly
            290                 295                 300

Thr Ser Thr Pro Ala Asn Glu Lys Gly Glu Ser Gly Ala Ile Val Ala
305                 310                 315                 320

Val Leu Gly Lys Glu Val Pro Val Ser Ser Thr Lys Ser Phe Thr Gly
            325                 330                 335

His Leu Leu Gly Ala Ala Gly Ala Val Glu Ala Ile Val Thr Ile Glu
            340                 345                 350

Ala Met Arg His Asn Phe Val Pro Met Thr Ala Gly Thr Ser Glu Val
            355                 360                 365

Ser Asp Tyr Ile Glu Ala Asn Val Val Tyr Gly Gln Gly Leu Glu Lys
370                 375                 380

Glu Ile Pro Tyr Ala Ile Ser Asn Thr Phe Gly Phe Gly Gly His Asn
385                 390                 395                 400

Ala Val Leu Ala Phe Lys Arg Trp Glu Asn Arg
            405                 410

<210> SEQ ID NO 3
<211> LENGTH: 25
<212> TYPE: DNA
<213> ORGANISM: Streptococcus pneumoniae

<400> SEQUENCE: 3
gctcctaaaa ggttactcca ccggc                                                25

<210> SEQ ID NO 4
<211> LENGTH: 431
<212> TYPE: PRT
<213> ORGANISM: Streptococcus pneumoniae -continued

<400> SEQUENCE: 4

```
Met Gly Ser Ser His His His His His His Ser Ser Gly Leu Val Pro
 1               5                  10                  15
Arg Gly Ser His Met Lys Leu Asn Arg Val Val Thr Gly Tyr Gly
            20                  25                  30
Val Thr Ser Pro Ile Gly Asn Thr Pro Glu Glu Phe Trp Asn Ser Leu
         35                  40                  45
Ala Thr Gly Lys Ile Gly Ile Gly Ile Thr Lys Phe Asp His Ser
     50                  55                  60
Asp Phe Asp Val His Asn Ala Ala Glu Ile Gln Asp Phe Pro Phe Asp
65                  70                  75                  80
Lys Tyr Phe Val Lys Lys Asp Thr Asn Arg Phe Asp Asn Tyr Ser Leu
                85                  90                  95
Tyr Ala Leu Tyr Ala Ala Gln Glu Ala Val Asn His Ala Asn Leu Asp
            100                 105                 110
Val Glu Ala Leu Asn Arg Asp Arg Phe Gly Val Ile Val Ala Ser Gly
            115                 120                 125
Ile Gly Gly Ile Lys Glu Ile Glu Asp Gln Val Leu Arg Leu His Glu
    130                 135                 140
Lys Gly Pro Lys Arg Val Lys Pro Met Thr Leu Pro Lys Ala Leu Pro
145                 150                 155                 160
Asn Met Ala Ser Gly Asn Val Ala Met Arg Phe Gly Ala Asn Gly Val
                165                 170                 175
Cys Lys Ser Ile Asn Thr Ala Cys Ser Ser Asn Asp Ala Ile Gly
            180                 185                 190
Asp Ala Phe Arg Ser Ile Lys Phe Gly Phe Gln Asp Val Met Leu Val
        195                 200                 205
Gly Gly Thr Glu Ala Ser Ile Thr Pro Phe Ala Ile Ala Gly Phe Gln
    210                 215                 220
Ala Leu Thr Ala Leu Ser Thr Thr Glu Asp Pro Thr Arg Ala Ser Ile
225                 230                 235                 240
Pro Phe Asp Lys Asp Arg Asn Gly Phe Val Met Gly Glu Gly Ser Gly
                245                 250                 255
Met Leu Val Leu Glu Ser Leu Glu His Ala Glu Lys Arg Gly Ala Thr
            260                 265                 270
Ile Leu Ala Glu Val Val Gly Tyr Gly Asn Thr Cys Asp Ala Tyr His
        275                 280                 285
Met Thr Ser Pro His Pro Glu Gly Gln Gly Ala Ile Lys Ala Ile Lys
    290                 295                 300
Leu Ala Leu Glu Glu Ala Glu Ile Ser Pro Gln Val Ala Tyr Val
305                 310                 315                 320
Asn Ala His Gly Thr Ser Thr Pro Ala Asn Glu Lys Gly Glu Ser Gly
                325                 330                 335
Ala Ile Ala Val Leu Gly Lys Glu Val Pro Val Ser Ser Thr Lys
            340                 345                 350
Ser Phe Thr Gly His Leu Leu Gly Ala Ala Gly Ala Val Glu Ala Ile
        355                 360                 365
Val Thr Ile Glu Ala Met Arg His Asn Phe Val Pro Met Thr Ala Gly
    370                 375                 380
Thr Ser Glu Val Ser Asp Tyr Ile Glu Ala Asn Val Val Tyr Gly Gln
385                 390                 395                 400
Gly Leu Glu Lys Glu Ile Pro Tyr Ala Ile Ser Asn Thr Phe Gly Phe
                405                 410                 415
```

-continued

```
Gly Gly His Asn Ala Val Leu Ala Phe Lys Arg Trp Glu Asn Arg
        420                 425                 430
```